US00PP36214P3

(12) United States Plant Patent
Pouillart

(10) Patent No.: US PP36,214 P3
(45) Date of Patent: Oct. 22, 2024

(54) ***ABELIA* PLANT NAMED 'Muabd'**

(50) Latin Name: ***Abelia* x *grandiflora***
Varietal Denomination: Muabd

(71) Applicant: Spring Meadow Nursery Inc., Grand Haven, MI (US)

(72) Inventor: Valérie Pouillart, Gien (FR)

(73) Assignee: Spring Meadow Nursery Inc.

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 18/109,592

(22) Filed: Feb. 14, 2023

(65) Prior Publication Data

US 2024/0276898 P1 Aug. 15, 2024

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02; A01H 5/00
See application file for complete search history.

(56) References Cited

PUBLICATIONS https://www.instagram.com/p/Cf8Vr2Eq6fV/; Jul. 13, 2022; 1 page.*
https://www.instagram.com/p/Ca17GSUqy6H/; Mar. 8, 2022; 1 page.*
https://newplants.nl/en/plants/abelia-grandiflora-jelly-beans/#:~:text=Jelly%20Beans%20is%20a%20new,white%2C%20bell%2Dshaped%20flowers.; Jun. 8, 2023; 2 pages.*
https://springmeadownursery.com/plantfinder/mucho-gusto-01650; Jun. 8, 2023; 3 pages.*
https://www.nurserymag.com/news/spring-meadow-nursery-introduces-new-proven-winners-colorchoice-varieties-for-2023-trade-shows/; Jan. 9, 2023; 3 pages.*
https://lgrmag.com/news/spring-meadow-nursery-introduces-new-varieties-for-2023-trade-shows/; Jan. 17, 2023; 3 pages.*
https://www.perishablenews.com/floral/spring-meadow-nursery-introduces-new-proven-winners-colorchoice-varieties-for-2023-trade-shows/; Jan. 9, 2023; 2 pages.*
In re Wingen; Feb. 2, 2023; 9 pages.*

* cited by examiner

*Primary Examiner* — Kent L Bell

(57) ABSTRACT

A new and distinct cultivar of *Abelia* plant named 'Muabd' is disclosed, characterized by yellow-green variegated foliage, abundant white flowers, and red colored stems. Plants have low rounded, slightly sprawling habits. The new variety is an *Abelia*, normally produced as an outdoor garden or container plant.

2 Drawing Sheets

Latin name of the genus and species: *Abelia* x *grandiflora*.
Variety denomination: 'MUABD'.

BACKGROUND OF THE INVENTION

The new *Abelia* cultivar is a product of chance discovery. The new variety was discovered as a naturally occurring single branch mutation on the parent variety, the unpatented *Abelia chinensis* 'Variegata'. The discovery of this new variety was made at a nursery in Gien, France during summer of 2016.

Asexual reproduction of the new cultivar 'Muabd' was first performed in summer of 2016 at a nursery in Gien, France. Vegetative soft wood cuttings were used. Subsequent propagation has shown that the unique features of this cultivar are stable and reproduced true to type in successive generations.

SUMMARY OF THE INVENTION

The cultivar 'Muabd' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Muabd'. These characteristics in combination distinguish 'Muabd' as a new and distinct *Abelia* cultivar:

1. Yellow-green variegated foliage with significant yellow-green new growth.
2. Rich flowering with white flowers; early flowering.
3. Red colored stems.
4. Foliage is resistant to disease and discoloration.

PARENT COMPARISON

Plants of the new cultivar 'Muabd' are similar to plants of the seed parent variety in most horticultural characteristics, however, plants of the new cultivar 'Muabd' differ in the following:

1. The new variety has yellow-green variegated foliage, while the parent has silver and green variegated foliage with a greater tendency to develop a pink blush at margins.
2. The new variety has a more open/sprawling habit, while the parent has a denser, more mounded habit.
3. The new variety has longer lateral branches than the parent.

COMMERCIAL COMPARISON

Plants of the new cultivar 'Muabd' can be compared to the variety *Abelia* 'Mincautri' U.S. Plant Pat. No. 33,457. These varieties are similar in most horticultural characteristics however, 'Muabd'differs in the following:

1. Variegated foliage of the new variety is predominately bi-colored, while variegated foliage of 'Mincautri' is predominately tri-colored.

BRIEF DESCRIPTION OF THE PHOTOGRAPHS

Figure 1:
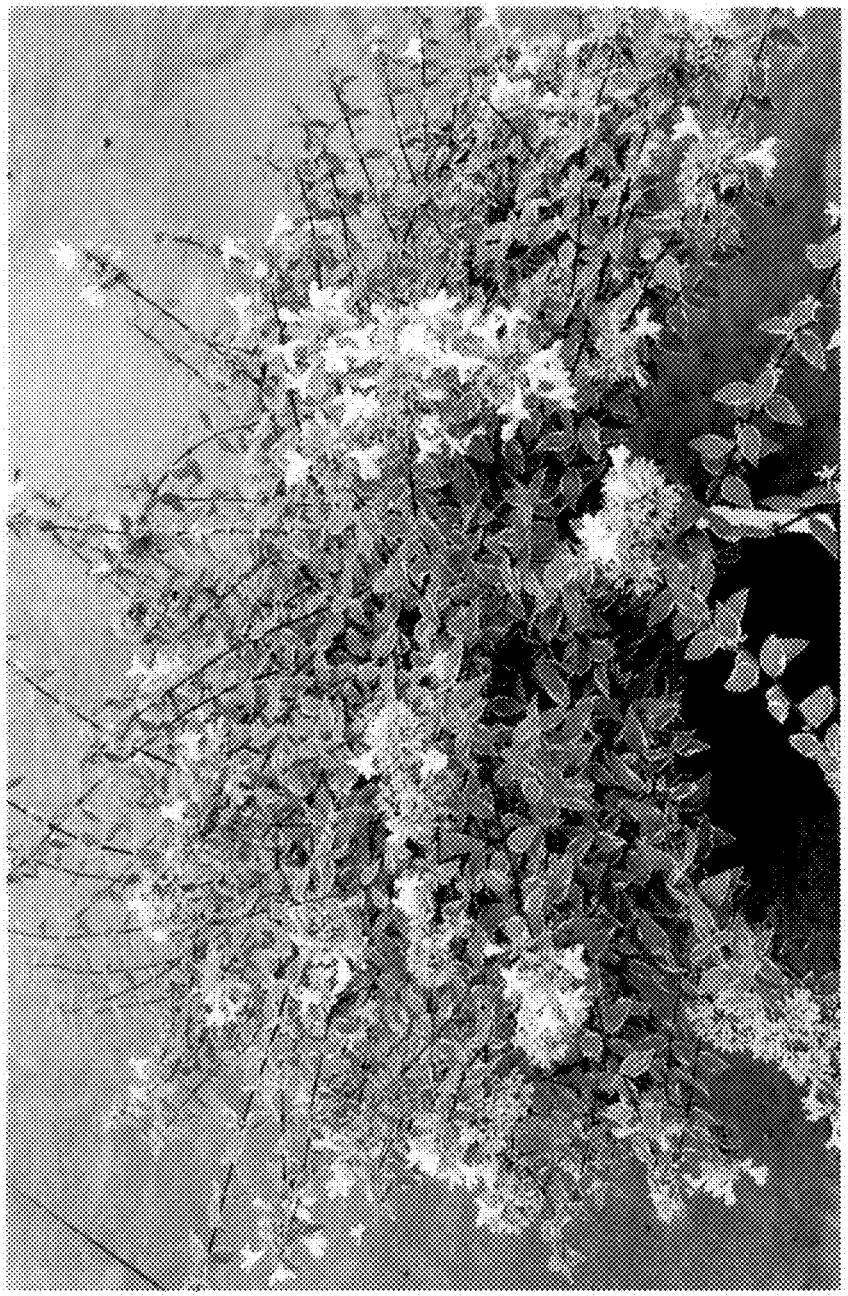

The accompanying photograph in FIG. 1 illustrates in full color a plant of 'Muabd' during the Summer grown outdoors, at approximately 2 years old.

Figure 2:
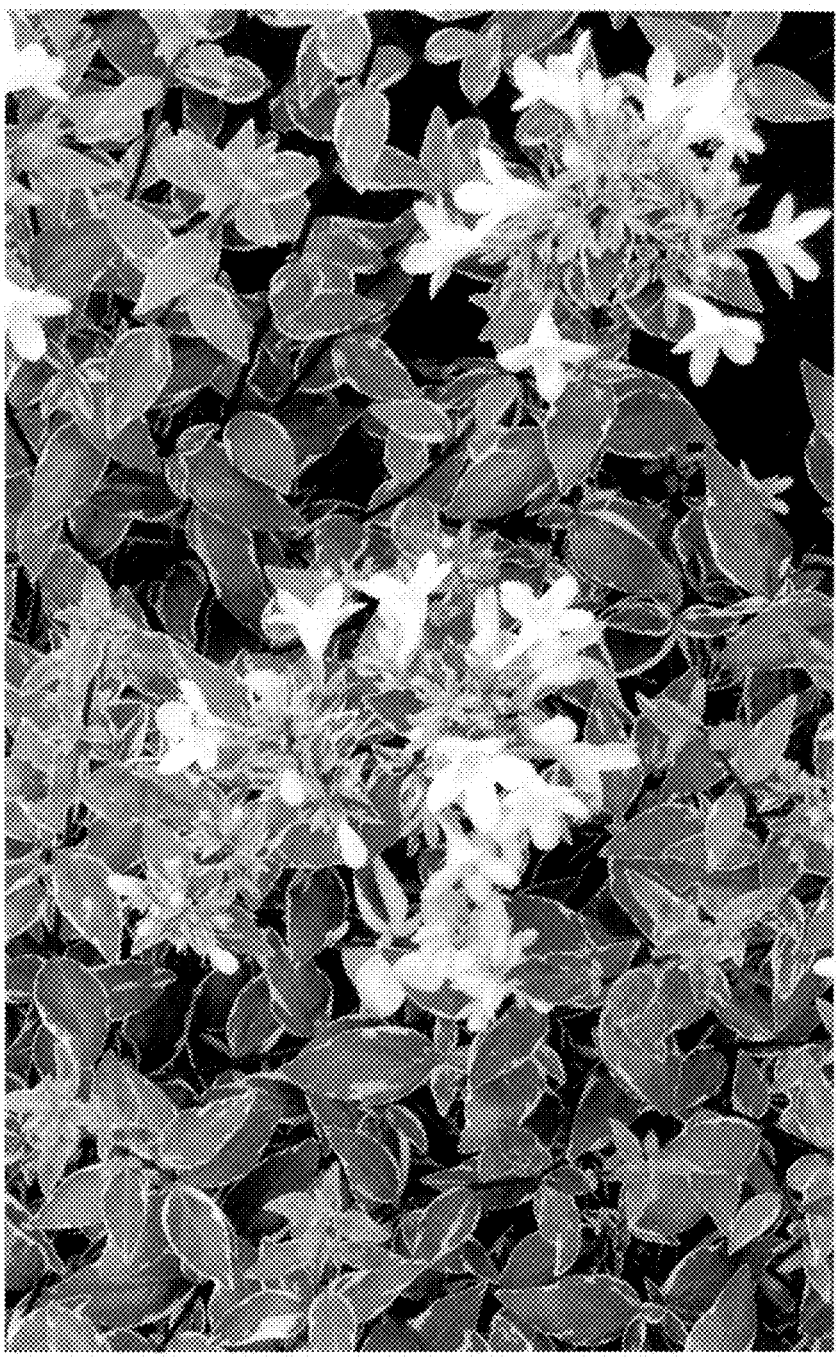

FIG. 2 illustrates a close-up view of foliage and inflorescences of 'Muabd'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe 'Muabd' plants grown in a polyhouse in Grand Haven, MI. Measurements were taken during June of 2022. The plants were about 2 to 3 years old in 3-gallon containers. The growing temperature ranged from approximately 18° C. to 27° C. during the day and 5° C. to 10° C. at night. Measurements and numerical values represent averages of typical plant types.

Botanical classification: *Abelia x grandiflora* 'Muabd'.

PROPAGATION

Time to initiate roots: 1 to 2 months at approximately 18 to 27° C. in the summer.

Time to produce a rooted young plant: About 40 days at approximately 18 to 27° C.

Root description: Moderately dense, freely branching, thin, fibrous, and fleshy. White to tan in color, not accurately measured by the color chart.

PLANT

Plant type: Perennial flowering shrub.
Age of plant described: 2 to 3 years old.
Growth habit: Rounded-semi-sprawling.
Pot size of plant described: 3-gallon pot.
Overall plant shape: Rounded.
Height: 35 cm.
Plant spread: 70 cm.
Plant vigor: Moderate.
Growth rate: Moderate.
Branching characteristics: Mixture of freely branching and some basal. Pinching required to encourage rounded shape.
Length of primary lateral branches: Average 30 cm.
Diameter of lateral branches: 2 mm.
Quantity of lateral branches: Average 25 to 30.

Stem:
- *Stem shape.*—Round.
- *Stem strength.*—Strong, slightly flexible.
- *Color.*—RHS Greyed-Red 178A.
- *Texture.*—Slightly pubescent.
- *Angle of attachment.*—45 to 90°.

Internode length: 3 cm on average.

FOLIAGE

Leaf:
- *Arrangement.*—Opposite.
- *Leaf shape.*—Lanceolate.
- *Average length.*—3.75 cm.
- *Average width.*—1.75 cm.
- *Apex.*—Acute to acuminate.
- *Base.*—Obtuse.
- *Margin.*—Entire.
- *Texture of top surface.*—Smooth, slightly waxy cuticle.
- *Texture of bottom surface.*—Glabrous with pronounced mid-rib.
- *Color.*—Young foliage upper side: RHS Yellow-Green 144A with N144A variegation along margin, appearing as a narrow, slightly irregular border about 1 mm wide. Young foliage under side: RHS Yellow-Green 144A with N144A variegation along margin, appearing as a narrow, slightly irregular border about 1 mm wide. Mature foliage upper side: RHS Yellow-Green 147A with Greyed-Yellow 160A variegation along margin, appearing as a narrow, slightly irregular border 1 to 2 mm wide. Mature foliage under side: RHS Yellow-Green 148B with Greyed-Yellow 160C variegation along margin, appearing as a narrow, slightly irregular border 1 to 231 mm wide.
- *Venation.*—Pattern: Pinnate. Color upper side: RHS Yellow-Green 148B. Color under side: RHS Yellow-Green 147A.
- *Petiole.*—Average Length: 2 mm. Diameter: 1 mm. Petiole color upper side: RHS Yellow-Green 147A with Greyed-Yellow 160A along margin. Petiole color lower side: RHS Yellow-Green 147B with Greyed-Yellow 160C along margin. Petiole Texture: Glabrous.

FLOWER

Natural flowering season: Late summer to early fall.
Flowering form: Single salverform flowers clustered at terminal ends of lateral branches.
Quantity of flowers per lateral stem: 5 to 10.
Quantity of buds per lateral stem: 5 to 10.
Quantity of flowers and buds per plant: 50 to 100.

Inflorescence:
- *Flowers per.*—15 to 20 flowers and buds per inflorescence.
- *Height.*—6 cm.
- *Diameter.*—9 cm.
- *Lastingness.*—3 to 5 weeks depending on environmental conditions.

Flower:
- *Depth.*—2 cm.
- *Diameter.*—2 cm.
- *Shape.*—Single whorl with 5 recurved petals.
- *Throat diameter.*—7 mm.
- *Throat/tube length.*—1.5 cm.
- *Throat texture.*—Glabrous.

*Throat color*.—RHS White NN155B.
*Tube diameter*.—2 mm.
*Tube texture*.—Glabrous.
*Tube color*.—RHS White NN155B.
*Aspect*.—Outward.
*Persistence*.—Self-cleaning.
*Fragrance*.—Slightly sweet.

Bud:
*Shape*.—Spatulate.
*Length*.—1.5 cm.
*Diameter*.—6 mm.
*Color*.—RHS Yellow 4C and 4D present individually.

Petal:
*Arrangement*.—Stellate.
*Number*.—5.
*Petal shape*.—Elliptic to oblong.
*Petal base*.—Fused.
*Margin*.—Entire.
*Tip shape*.—Obtuse.
*Length from throat*.—7.5 mm.
*Width*.—5 mm.
*Texture*.—Upper: Smooth, pubescent. Lower: Soft, smooth. Appearance: Smooth, soft.

Color:
*When opening*.—Inner surface: RHS White NN155B. Outer surface: RHS White NN155B.
*Fully opened*.—Upper surface: RHS White NN155B. Lower surface: RHS White NN155B.
*Vein color*.—Upper surface: RHS White NN155B. Lower surface: RHS White NN155B. Vein color, tube: RHS White NN155B.

Sepal:
*Arrangement*.—Whorl.
*Number*.—Average 5.
*Shape*.—Narrowly elliptic.
*Tip*.—Acute.
*Base*.—Attenuate.
*Margin*.—Entire.
*Length*.—7 mm.
*Width*.—2 mm.
*Texture, upper*.—Smooth.
*Texture, lower*.—Smooth.
*Color*.—Upper surface: RHS Yellow-Green 144B with White 155B variegated margins becoming Red 39C, especially after flower is shed. Lower surface: RHS Yellow-Green 144B with White 155B variegated margins 23 becoming Red 39C, especially after flower is shed.
*Calyx shape*.—Collar-like.

Peduncle:
*Length*.—5 mm.
*Diameter*.—2 mm.
*Color*.—RHS Yellow-Green 144B.
*Orientation*.—About 45°.
*Strength*.—Good.
*Texture*.—Glabrous.

Pedicel: Not present.

REPRODUCTIVE ORGANS

Stamens:
*Number*.—Average 4.
*Filament length*.—1 cm.
*Filament color*.—RHS White 155B.

Anthers:
*Shape*.—Linear.
*Length*.—2 mm.
*Color*.—RHS Greyed-Yellow 162D.
*Pollen color*.—RHS Greyed-Yellow 162D.
*Pollen amount*.—Sparse to moderate.

Pistil:
*Number*.—1.
*Length*.—1 cm.
*Style*.—Length: 9 mm. Color: RHS White 155B.
*Stigma*.—Shape: Rounded/globose. Color: RHS Greyed-Yellow 162D.

OTHER CHARACTERISTICS

Seeds and fruits: Not observed.

Disease/pest resistance: Neither resistance nor susceptibility to normal diseases and pests of *Abelia grandiflora* have been observed.

Temperature tolerance: Typical range USDA zones 5 through 9.

What is claimed is:

1. A new and distinct cultivar of *Abelia* plant named 'Muabd' as herein illustrated and described.

* * * * *